United States Patent
Göbel et al.

(10) Patent No.: US 10,723,985 B2
(45) Date of Patent: Jul. 28, 2020

(54) PHOTOBIOREACTOR WITH MATS MADE FROM LIGHT-DECOUPLING OPTICAL FIBRES AND ELECTRICALLY CONDUCTIVE FIBRES GENERATING A TRAVELLING ELECTRIC FIELD

(71) Applicant: Airbus Defence and Space GmbH, Taufkirchen (DE)

(72) Inventors: Johann Göbel, München (DE); Jennifer Wagner, München (DE); Robert Schreiber, Gräfelfing (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 529 days.

(21) Appl. No.: 15/100,079

(22) PCT Filed: Nov. 26, 2014

(86) PCT No.: PCT/DE2014/100416
§ 371 (c)(1),
(2) Date: May 27, 2016

(87) PCT Pub. No.: WO2015/078451
PCT Pub. Date: Jun. 4, 2015

(65) Prior Publication Data
US 2017/0198244 A1    Jul. 13, 2017

(30) Foreign Application Priority Data
Nov. 28, 2013    (DE) .................. 10 2013 019 889

(51) Int. Cl.
*D03D 15/00*    (2006.01)
*C12M 1/00*    (2006.01)
(Continued)

(52) U.S. Cl.
CPC ............... *C12M 21/02* (2013.01); *A01G 7/04* (2013.01); *A01G 31/00* (2013.01); *A01G 33/00* (2013.01);
(Continued)

(58) Field of Classification Search
CPC ........ G02B 6/001; G02B 6/04; G02B 6/4479; C12M 21/02; C12M 31/08; C12M 23/26;
(Continued)

(56) References Cited

U.S. PATENT DOCUMENTS

2006/0144460 A1 * 7/2006 Brochier ............... D03D 15/00
139/420 C
2010/0021124 A1 * 1/2010 Koos ....................... G02F 1/011
385/141

(Continued)

FOREIGN PATENT DOCUMENTS

CN    1867712 A    11/2006
CN    102382754 A    3/2012
(Continued)

OTHER PUBLICATIONS

German Patent Office, German Search Report for German Patent Application No. 10 2013 019 889.5 dated Sep. 29, 2014.
(Continued)

*Primary Examiner* — Robert H Muromoto, Jr.
(74) *Attorney, Agent, or Firm* — Nixon & Vanderhye P.C.

(57) ABSTRACT

A photobioreactor is described for cultivating phototrophic organisms and in particular a mat, as can be used in one such photobioreactor. The mat has a plurality of first fibres which are light conductive along their longitudinal direction and are constructed to decouple light conducted in the longitudinal direction laterally, at least somewhat transversely to the longitudinal direction. The mat furthermore has a plurality of second fibres which are electrically conductive
(Continued)

along their longitudinal direction. With the aid of one such mat, light can on the one hand be coupled in the interior of a photobioreactor. On the other hand, a travelling electric alternating field can be generated by applying a suitable polyphase voltage from a voltage source with the aid of electrically conductive second fibres. This alternating field can act on electrically charged particles.

18 Claims, 3 Drawing Sheets

(51) Int. Cl.
    *A01G 7/04*     (2006.01)
    *A01G 31/00*     (2018.01)
    *A01G 33/00*     (2006.01)
    *C12M 1/26*     (2006.01)
    *D03D 1/00*     (2006.01)

(52) U.S. Cl.
    CPC ............ *C12M 31/08* (2013.01); *C12M 33/00* (2013.01); *C12M 43/08* (2013.01); *D03D 15/00* (2013.01); *D03D 15/0027* (2013.01); *D10B 2101/12* (2013.01); *D10B 2401/16* (2013.01); *D10B 2401/20* (2013.01)

(58) Field of Classification Search
    CPC .. C12M 31/10; B32B 2262/103; B32B 5/024; B32B 2307/206; H01B 13/0165; H01B 9/005; H01B 11/22; H01B 13/067; H01B 3/30; H01B 3/47; H01B 7/02; H01B 7/1855
    See application file for complete search history.

(56) References Cited

U.S. PATENT DOCUMENTS

| | | | |
|---|---|---|---|
| 2012/0090874 A1* | 4/2012 | Pagliuca | B32B 5/16 174/120 SR |
| 2012/0091002 A1* | 4/2012 | Taylor | B01D 57/02 204/547 |
| 2013/0092543 A1* | 4/2013 | Heikenfeld | A47L 13/16 204/554 |
| 2013/0102076 A1* | 4/2013 | Licamele | C12M 21/02 435/420 |
| 2013/0202259 A1* | 8/2013 | Varkey | H01B 13/225 385/101 |
| 2015/0117825 A1* | 4/2015 | Burke | H01B 11/22 385/101 |
| 2015/0170791 A1* | 6/2015 | Varkey | H01B 7/046 174/106 R |
| 2015/0170799 A1* | 6/2015 | Varkey | G02B 6/4416 174/70 R |
| 2015/0219867 A1* | 8/2015 | Ruan | G02B 6/4416 385/101 |
| 2016/0069009 A1* | 3/2016 | Meer | B29C 70/24 428/102 |
| 2016/0201020 A1* | 7/2016 | Gobel | C12M 21/02 435/292.1 |
| 2017/0368790 A1* | 12/2017 | DeCoste | G01M 3/3272 |

FOREIGN PATENT DOCUMENTS

| | | |
|---|---|---|
| DE | 102007018675 A1 | 10/2008 |
| DE | 10 2010 025 366 A1 | 12/2011 |
| EP | 2 520 642 A1 | 11/2012 |
| WO | 2008145719 A1 | 12/2008 |

OTHER PUBLICATIONS

People's Republic of China, Chinese Office Action for Chinese Patent Application No. 201480065330.7 dated Mar. 15, 2017.
International Searching Authority, International Search Report for International Patent Application No. PCT/DE2014/100416 dated Mar. 27, 2016.

\* cited by examiner

PHOTOBIOREACTOR WITH MATS MADE FROM LIGHT-DECOUPLING OPTICAL FIBRES AND ELECTRICALLY CONDUCTIVE FIBRES GENERATING A TRAVELLING ELECTRIC FIELD

CROSS-REFERENCE TO RELATED APPLICATIONS

This is a continuation of International Application No. PCT/DE2014/100416, filed Nov. 26, 2014, which application claims priority to German Application No. 10 2013 019 889.5, filed Nov. 28, 2013, which are hereby incorporated by reference in their entirety.

TECHNICAL FIELD

The embodiments described herein relate to a photobioreactor for cultivating phototrophic organisms. Furthermore, the embodiment relates to mats made of fibres and also a mat device having such mats, as can be used advantageously in a photobioreactor.

BACKGROUND

Phototrophic organisms are microbes, e.g. in the form of micro-organisms, which can use light directly as an energy source for their metabolism. For example, phototrophic organisms include certain plants, mosses, micro-algae, macro-algae, cyanobacteria and purple bacteria.

It may be desirable for different use purposes to be able to produce biomass, for example in the form of algae, in large quantities and inexpensively. For example, such biomass can be used for creating alternative biofuels, e.g. for the transport sector.

So-called bioreactors are used in order to be able to create biomass on an industrial scale. A bioreactor is a plant for producing organisms outside of their natural environment and within an artificial technical environment. So-called photobioreactors are used in order to cultivate phototrophic organisms. A photobioreactor provides the phototrophic organisms with both light and $CO_2$ and a suitable nutrient solution, if appropriate, so that the phototrophic organisms can correspondingly create biomass.

In general, both open and closed systems are known for photobioreactors. Each of these types of photobioreactors has certain advantages and disadvantages.

In open photobioreactor systems, sometimes also refers to as open ponds, phototrophic organisms are cultivated in a controlled manner in open reservoirs or ponds. In this case, for the most part, a nutrient solution or culture suspension, which contains all of the required nutrients for the relevant organism and $CO_2$, is conveyed in a circuit and illuminated for the most part directly by the sun from the open surface.

Possible advantages of such open photobioreactor systems are a relatively small technical outlay and low power consumption.

However, illumination solely by means of the upwardly open surface entails that only small volumes can be supplied with sufficient light. For the most part, light can only penetrate to a depth of a few centimetres into a nutrient solution to which organisms have been added. The depth of such open photobioreactor systems is therefore generally limited to 20 to 30 cm. The low average light influx leads to low areal growth rates. Thus, a large area must be provided for open photobioreactor systems. As a result, costs are increased considerably for such photobioreactors, particularly in densely populated regions.

In addition, pronounced evaporation and therefore salinity effects may result at the exposed surface. Furthermore, a considerable quantity of $CO_2$ can also diffuse into the atmosphere via the exposed surface. Conversely, contaminants may enter an open photobioreactor via the exposed surface, contaminate the photobioreactor and therefore jeopardise product purity. Furthermore, any heating or cooling of such open photobioreactor systems that may be required is difficult to design. In the case of illumination exclusively with sunlight, a daytime dependence also results, deeper layers often only being illuminated unsatisfactorily, whereas directly at the surface of the open system very high illumination intensities may occur which may, where appropriate, lead to what is known as photoinhibition.

The sum of the mentioned disadvantages or limiting boundary conditions can in particular lead to it often only being possible to use open photobioreactor systems in the form of open ponds all year round in very particular geographical areas.

Closed photobioreactor systems were developed in order to reduce an influence of environmental conditions on the one hand and to achieve a higher yield during the cultivation of phototrophic organisms on the other hand. In such closed systems, a nutrient solution is conveyed through a closed circuit together with the organisms and for the most part is illuminated from outside.

For example, in a pipe photobioreactor, glass or plastic pipes are combined to form a closed circuit and the organisms enclosed therein are supplied with nutrients and $CO_2$ by means of a central unit which for example can contain suitable pumps and sensors.

Closed photobioreactors generally allow a high degree of process control, because the organisms and the surrounding nutrient solution can be heated or cooled well in the closed system, a pH value can be monitored and adjusted if necessary, and additional light can be provided. The closed systems allow a high productivity for a low area requirement, because for example a plurality of closed systems can be arranged above one another or pipes of one system can run in the vertical direction and can thereby be illuminated from all sides. However, shadow effects are always to be expected. In addition, high product purity with low contamination, low evaporation and low electromagnetic interference (EMC) is also possible.

However, technical outlay and corresponding plant investment costs when building complex closed photobioreactors are generally very high compared to open systems.

A multiplicity of technical solutions has already been developed to increase the efficiency of photobioreactors. A measure for the efficiency of a photobioreactor can here be understood to be the quantity of necessary resources, such as for example energy to be supplied in the form of light and/or electricity, area to be provided, nutrients to be provided, etc. in relation to the yield of the photobioreactor in the form of biomass with quantities as high as possible of energy chemically stored therein.

For example, a photobioreactor with rotationally oscillating light sources was described in EP 2 520 642 A1.

SUMMARY

It may be considered to be an object of the present embodiment to provide a photobioreactor for cultivating phototrophic organisms, which enables a high efficiency for low plant investment costs and/or low operating costs. In particular, it may be desired to be able both to efficiently supply phototrophic organisms within a photobioreactor with light and to move the phototrophic organisms or a nutrient solution accommodating the same in a targeted fashion, for example, in order to ensure thorough mixing or to be able to remove, i.e. "to harvest", the phototrophic organisms from the photobioreactor in a targeted fashion. Furthermore, it may be desired to provide components for a bioreactor which enable these advantages.

These objects can be achieved by means of a photobioreactor, a mat or a mat arrangement according to the independent claims. Advantageous embodiments are specified in the dependent claims and in the following description.

Ideas for embodiments of the photobioreactor according to an embodiment can, inter alia, be considered as being based on the following ideas and discoveries:

Phototrophic organisms should be supplied with light and nutrients as well as possible for their cultivation. However, in a nutrient solution which is densely populated with organisms, light can only propagate over very short distances of a few centimetres. A photobioreactor in which the nutrient solution is accommodated in a container and the container is only illuminated from outside must therefore provide an illuminable outer surface which is as large as possible while having a relatively small volume. This is associated with the necessity of supplying a large base surface for the photobioreactor, as for example in the case of an open pond system, or a complex structural design, as for example in the case of conventional closed systems such as pipe photobioreactors.

In accordance with the embodiments, it is now suggested to arrange one or a plurality of special mats in a container of a photobioreactor which accommodates the nutrient solution. In this case the mat contains fibres which are specifically constructed to decouple light which is coupled in at the ends thereof not only at oppositely located ends of the fibres but rather laterally, that is to say transversely to a surface of the light guide mat. The light decoupling can take place as homogeneously as possible over an entire surface of the light guide mat. Therefore, it can be achieved that large quantities of light can be introduced in the interior of the container of the photobioreactor in a substantially homogeneously distributed manner over the surface of the light conductive mat. By using the at least one laterally light-decoupling mat, a high efficiency and also possibly further advantages which are to be described in more detail below can be achieved for the suggested photobioreactor.

The mat should furthermore include fibres, which are electrically conductive. Electric fields can be effected in a targeted fashion along a surface of the mat by applying electric voltages to these fibres in a controlled manner. Such electric fields can be utilised in order to move charged particles or components in a targeted fashion or convey the same in one direction.

For example, in an illuminated solution the phototrophic organisms themselves are for the most part present in an electrically charged state, so that the same can be moved under the action of an electric field. In this manner, the phototrophic organisms can for example be mixed thoroughly in the photobioreactor and/or conveyed to a region of the photobioreactor from which they can then be removed, that is to say "be harvested".

A mat consisting of various fibres can therefore be used in a photobioreactor both to couple light into the interior of the photobioreactor and to thoroughly mix or harvest the phototrophic organisms inside the photobioreactor.

According to a first aspect, a mat is suggested which has a plurality of first fibres and a plurality of second fibres. The first fibres are light conductive along their longitudinal direction and constructed to decouple light conducted in the longitudinal direction laterally, at least partially transversely to the longitudinal direction. The second fibres are electrically conductive along their longitudinal direction.

In this case, a mat can be understood to mean a flat, thin structure in which a plurality of fibres are mechanically connected to one another. The mat can be constructed for example as a woven fabric, mesh or knitted fabric. The mat can be mechanically flexible and in particular bendable transversely to its area of extent.

A fibre can be understood to mean a structure which is thin and flexible in relation to its length. Fibres can consist of a wide range of materials. Due to the low thickness of a typical fibre, materials which are normally hard or brittle at larger masses can also be used without the flexibility of the fibre being impaired. In particular, fibres can consist of glass, carbon, plastics or metals. Even wires, strands, etc. consisting of metal should be considered to be fibres in this context.

The first fibres should consist, at least in the core thereof, of a material which is substantially transparent for light, particularly for light in a wavelength range of 300 nm to 1200 nm, particularly 400 nm to 800 nm. In a manner orientated to the intended purpose, the optical transparency should be sufficiently high in this case so that light can be conducted from one end of the fibre through the fibre to its destination without significant absorption losses, that is to say with absorption losses of for example less than 20%. In particular, the first fibres can be constructed as glass fibres or polymer fibres made from a transparent polymer.

The second fibres can have the same or different diameters as the first fibres and/or can be constructed at least to some extent from the same materials as the first fibres. However, the second fibres should at least additionally be constructed using a material which effects an electrical conductivity along the longitudinal direction of the second fibres.

For example, the second fibres can be constructed as carbon fibres, as are also used for producing CFK fabrics. Such carbon fibres can be processed easily and are chemically resistant. In particular carbon fibres are also suitable for use in a photobioreactor due to their suitability for splitting water (graphite) into hydrogen and oxygen atoms or molecules, respectively. In addition, carbon fibres generally do not form any metal ions in an algae nutrient solution which can be a decisive advantage in process optimisation in the case of use in a photobioreactor, because metal ions can act toxically and generally have a negative effect and may be troublesome during a later recovery of algae as a raw material.

Alternatively or additionally, the second fibres can be constructed using an electrically conductive polymer. Such electrically conductive polymers can generally be processed well and are chemically resistant.

Furthermore alternatively or additionally, the second fibres can be constructed using a precious metal. For example, they can be constructed as precious-metal wire. Metal fibres of this type generally have a high chemical resistance and strong optical reflectivity, as a result of which they can act, for example in the case of use in a photobioreactor, as a mirror on the fibre rear side for improved light decoupling on an opposite bent light side of a light conductive fibre.

In a further design, the second fibres can be constructed in a radially internal region using an electrically insulating material and can be coated using an electrically conductive layer in a region that is located radially further out. In other words, it is not necessary for the entire second fibre to consist of an electrically conductive material, rather it may be sufficient to coat only a part region, for example a surface of the fibres, with an electrically conductive material. For example, a fibre that consists of an electrically insulating material at the core can be coated with a thin metal layer.

In a further design, the second fibres can be configured such that they are light-conductive in a radially internal region and are coated with an electrically conductive and optically transparent layer in a region which is located radially further out. Second fibres configured in this manner can be used both to conduct light and decouple the same at a destination, and to convey electric power or generate electric fields. For example, a second fibre can be constructed at its core as a glass fibre. An optically transparent layer for example made from zinc oxide, tin oxide or indium oxide can be constructed on a surface of a second fibre, which layer has sufficiently high electrical conductivity.

The first and second fibres can be interwoven with one another to form a mat. In other words, the first and second fibres can form a woven mat. The first fibres in this case can be interwoven as warp threads and the second fibres can be interwoven as weft threads or vice versa. In a woven fabric, the first and second fibres are in a regularly ordered arrangement. In this case, the first fibres run transversely, generally approximately perpendicularly to the second fibres. In a woven fabric, the first and second fibres are connected to one another in a stable manner, so that a mat of this type can be handled and processed easily.

In the mat, the second fibres can preferably be arranged parallel to one another. In a mat designed as a woven fabric, the second fibres can for example run parallel to one another as warp threads in each case or as weft threads in each case. An electric field generated using such parallel second fibres can be particularly homogeneous or linear.

According to a design, the plurality of second fibres can have at least one first, one second and one third subgroup of second fibres. The subgroups in this case are electrically insulated from one another. The fibres of each subgroup can preferably be combined to form a plurality of bundles, wherein in particular each bundle of fibres of a subgroup can be arranged and/or constructed in a manner electrically insulated from a bundle of fibres of a different subgroup.

In a design of this type, the plurality of second fibres of the first, second and third subgroup can be arranged in a cyclical pattern. For example, a fibre or a bundle of fibres of the second subgroup can be arranged parallel to fibres or a bundle of fibres of the first group, and parallel to the same in turn a fibre or a bundle of fibres of the third subgroup, before then a fibre or a bundle of fibres of the first subgroup follows again, etc.

According to a second aspect of the embodiment, a mat arrangement is suggested which has a configuration of the above-described mat and also an electric voltage source which is electrically connected to the second fibres of this mat.

The voltage source can in this case have at least three electrodes, wherein the plurality of second fibres in turn can be divided into a first, a second and a third subgroup of second fibres and these subgroups can be electrically insulated from one another. In a design of this type, each of the subgroups can be electrically connected to only one of the electrodes and the voltage source can for example be configured to generate a polyphase current in the second fibres connected to the electrodes. In this case, a polyphase current can be understood to mean a multi-phase alternating current which consists of a plurality of, for example three, individual alternating currents or AC voltages of the same frequency, which are fixedly shifted with respect to one another in terms of their phase angles, for example by 120°. A polyphase current generated in the second fibres in this manner can generate cyclically varying electric fields adjacently to the fibres, in particular a travelling electric alternating field can be generated.

According to a further embodiment, a photobioreactor for cultivating phototrophic organisms is suggested which has a container and also one of the previously described mat arrangements. In this case, the container is constructed to accommodate the phototrophic organisms together with a nutrient solution. The mats of the mat arrangement are arranged inside the container.

In a photobioreactor of this type, the mat arrangement can on the one hand be used to feed light of an outer light source through the first fibres of the mats into the interior, that is to say into the nutrient solution accommodated in the container and therefore to supply the phototrophic organisms. On the other hand, suitable electric voltages or currents can be generated by means of the electric voltage source of the mat arrangement in the second fibres, in order to generate temporally varying electric fields adjacently to the mats, with the aid of which electrically charged constituents of the nutrient solution or electrically charged phototrophic organisms themselves can be moved.

In one design, the voltage source can be configured to generate a polyphase current in the second fibres connected to the electrodes in such a manner that a travelling electric alternating field is generated adjacently to the associated mat, the travelling direction of which for example is directed to a harvest region of the photobioreactor. In other words, the electric voltages to be applied by the voltage source to the second fibres can be controlled in such a manner that the electric fields generated by the second electric fibres vary temporally and spatially in such a manner that in total a travelling electric alternating field results. In such a travelling electric alternating field, regions of the same electrical potential move continuously and preferably with a constant travel direction. In this case, the voltage source can be controlled in such a manner that the travel direction leads to a region of the photobioreactor from which matured phototrophic organisms can be removed from the photobioreactor, that is to say be harvested.

It is pointed out that possible advantages and features of embodiments are described herein to some extent with reference to a photobioreactor according to an embodiment and to some extent with reference to a mat or mat arrangement according to a further embodiment. A person skilled in the art will recognise that the various features can be combined, transferred or exchanged in a suitable manner in order to realise further embodiments.

BRIEF DESCRIPTION OF THE DRAWINGS

The various embodiments will hereinafter be described in conjunction with the following drawing figures, wherein like numerals denote like elements, and.

The figures are only schematic and not true to scale. Identical reference numbers in the different figures designate identical or identically acting features.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1:
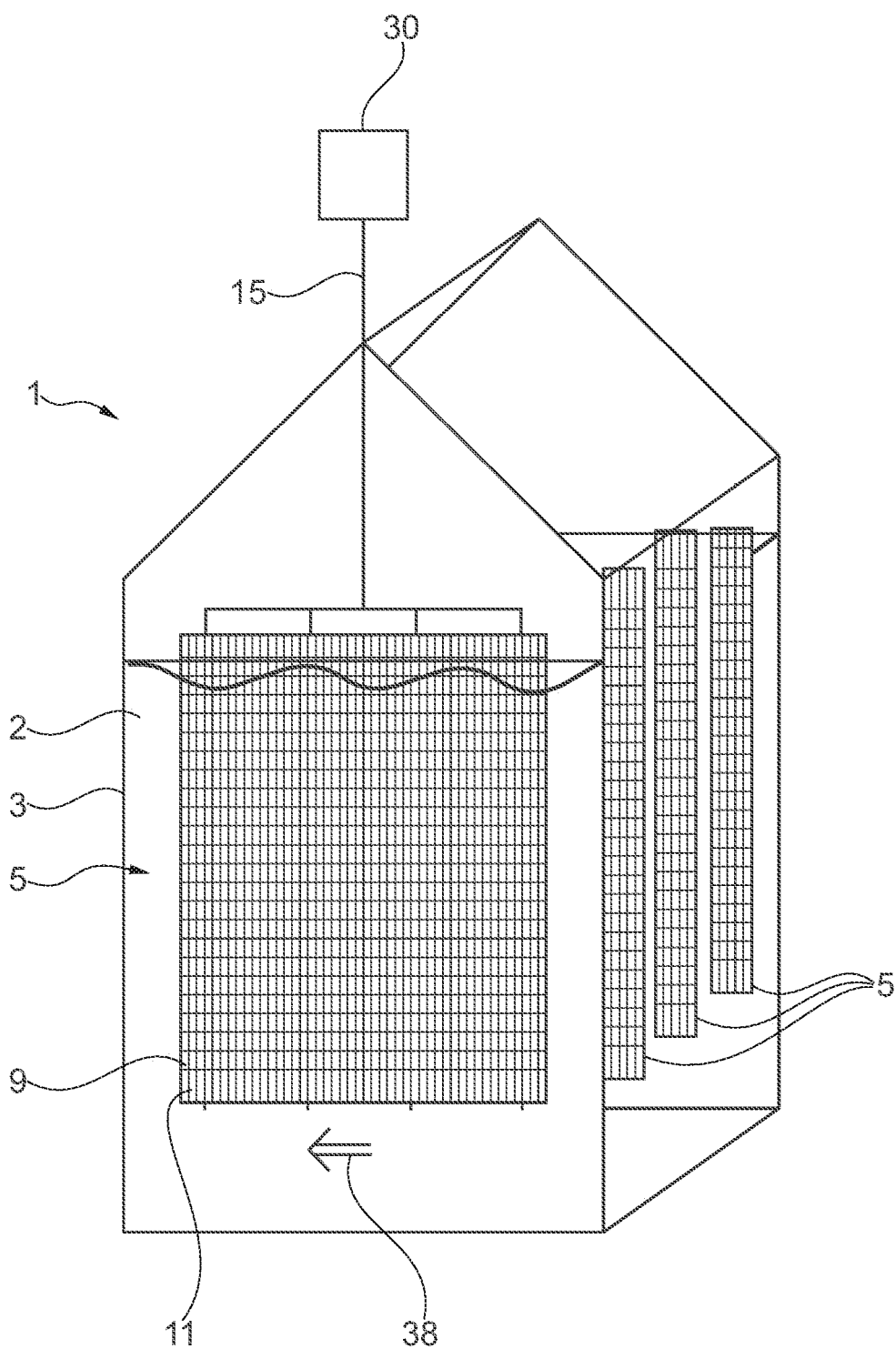
FIG. 1 shows a photobioreactor according to an embodiment

FIG. 1 shows a schematic perspective view of a photobioreactor 1 according to an embodiment. The photobioreactor 1 has a container 3 in which phototrophic organisms can be accommodated together with a nutrient solution 2. A plurality of mats 5 are arranged virtually parallel to one another and spaced from one another in the container 3. Each of the mats 5 is constructed using a multiplicity of first light conductive fibres 9, which are arranged and constructed in such a manner that light which is for example coupled into ends of the fibres 9 by means of a common light guide 15 that is guided out of the container 3, at least to some extent exits from the fibres 9 laterally and therefore transversely to the surface of the mats 5. Each mat 5 furthermore has a multiplicity of second fibres 11 which are electrically conductive along their longitudinal direction.

The container 3 may have any desired geometry. For example, the container, as illustrated in FIG. 1, can be configured to be cuboidal or cubic. Alternatively, the container 3 can also be constructed cylindrically, spherically or with a different shape.

In this case, the container 3 can have a suitable geometry, wherein the container 3 can accommodate a large volume while at the same time having a relatively small surface. In particular, a depth of the container 3 can be larger than lateral dimensions or the base area of the container 3. The depth of the container 3 should in this case be measured in a direction transverse to a main plane of extent of the light guide mat. In particular, the container 3 can have dimensions of more than 50 cm, preferably more than 1 m in each spatial direction, that is to say in height, width and depth.

At least in a bottom region, the container 3 should be realised in a sealed manner so that liquid nutrient solution 2 together with the phototrophic organisms accommodated therein can be held in the container 3. In a top region, the container 3 can, as illustrated in FIG. 1, likewise be realised to be closed and sealed, so that an inherently closed photobioreactor 1 is formed. Alternatively, the container 3 can indeed also be open at the top in order to form an open photobioreactor. Walls of the photobioreactor 1 (only edges are reproduced in FIG. 1 for a better overview, in order to enable internal components of the photobioreactor to be seen) can be constructed from any desired fluid-tight materials, such as for example plastic or metal, and do not necessarily have to be light-permeable.

Each of the mats 5 can be composed of a multiplicity of light-conductive first fibres 9 and electrically conductive second fibres 11. In this case the first fibres 9 can be connected to one another and to the second fibres 11 in a different manner securely or loosely. The mat 5 can for example be provided in the form of a woven fabric, a knitted fabric, a fleece or a different 2- or 3-dimensional structure, for example a honeycomb structure. In this case the mat 5 is constructed to be for example flat, wherein a thickness transverse to the main direction of extent of the surface can be less than 10 mm, preferably less than 2 mm. The mat is inherently flexible and bendable and correspondingly has similar mechanical properties to a film. However, the mat 5 is fluid-permeable since it consists of a multiplicity of fibres, that is to say fluid, for example in the form of the nutrient solution, can slowly flow through the mat 5.

The first fibres 9 forming a part of the mat 5 conduct light well, at least in the interior thereof, that is to say in a core, that is to say they have a high optical transparency. The fibres can consist of transparent materials, such as for example glass or a transparent plastic, particularly a transparent polymer such as PMMA (polymethyl methacrylate). The first fibres 9 or cores of the first fibres 9 can have diameters in the range of a few micrometres up to a few millimetres. Typical diameters are in the range of 0.25 to 2 mm, particularly 5 to 30 µm. Each of the first fibres 9 can be very bendable and be curved, for example with radii of curvature of less than 10 mm.

In order to be able to conduct light in the interior of the first fibre 9, the first fibre 9 can be encapsulated with a layer termed "cladding", which has a lower optical refractive index than a material in the core of the first fibre 9. Light impinging onto cladding of this type at flat angles is fed back into the core of the fibre by total internal reflection and can therefore propagate over long distances in an elongated fibre.

However, for the specific use of mats 5 in a photobioreactor, it is also possible to provide light conductive fibres without such a cladding, because it is assumed that the nutrient solution surrounding the individual fibres may likewise have a suitable optical refractive index, so that the desired total internal reflection occurs.

The light conductive first fibres 9 can be constructed with a surface which is as smooth as possible in order to prevent deposits or dirt from adhering to individual fibres. If necessary, the fibres can be coated in a hydrophobic manner, for example covered with a coating made from titanium dioxide ($TiO_2$). Even a coating with a material that increases scratch resistance can be provided. Any coatings can be applied for example using plasma processes, a sol/gel technology or by painting.

As will be explained in more detail below on the basis of actual exemplary embodiments, the mats 5 or the light conductive first fibres 9 used therein are configured in such a manner that light conducted in the first fibres 9 is decoupled laterally to some extent, that is to say transversely to a surface of the light guide mat 5. A component of the laterally exiting light should in this case be considerable in relation to a total quantity of the light exiting from the fibres 9 of the light guide mat 5, for example at least 10%, preferably however at least 50%, possibly even at least 90%. A portion of light exiting laterally from the light guide mat 5 can in this case exit laterally from the mat 5, preferably homogeneously distributed over the same. In other words, light coupled into an individual first fibre 9 can exit from the first fibre laterally along the entire length of the same, thereby being distributed to the greatest extent possible.

Figure 2:
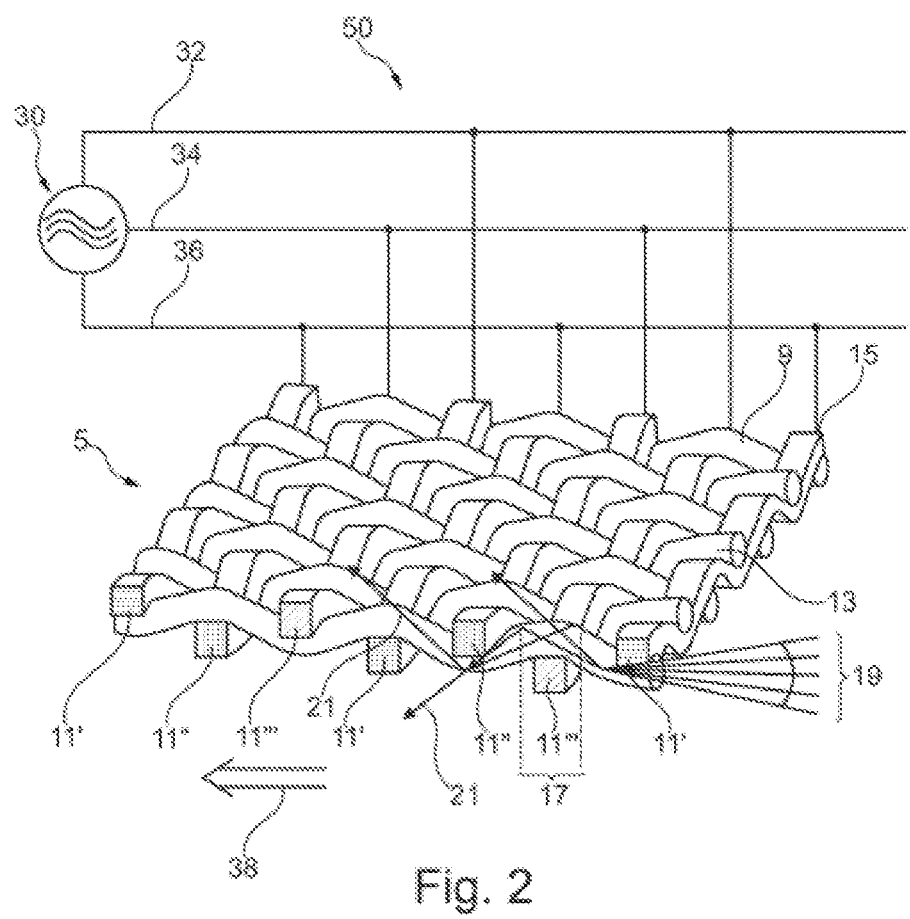
FIG. 2 shows a cut-out of a mat arrangement according to an embodiment.

FIG. 2 shows a mat arrangement 50 having a mat 5 in which a multiplicity of light conductive first fibres 9 and electrically conductive second fibres 11 are interwoven with one another to form a woven fabric. The fibres 9, 11 of the woven fabric can in this case be interwoven with one another in various web patterns. In this case, the first fibres 9 can form the warp threads 13 running in the longitudinal direction and the second fibres 11 can form the weft threads 15 running in the transverse direction, or vice versa.

Due to the interwoven structure, in this case the light conductive first fibres 9 are locally curved in such a manner that at least in regions 17 with minimum radius of curvature parts of the light 19 coupled into a first fibre 9 and conducted in the same in the longitudinal direction of the fibre are decoupled from the fibre 9 laterally. The decoupled portions of light 21 are radiated transversely to the direction of extent of the mat 5 and can therefore illuminate adjacent volumes inside the container 3 of the photobioreactor 1.

Lateral decoupling of light out of individual light conductive fibres 9 can also be achieved in that local refractive-index variations are formed in the light conductive first fibres 9. In other words, the first fibres 9 are produced or processed in such a manner that light which propagates in the interior of the first fibres along the length thereof runs through regions with different refractive indices or strikes such regions.

The refractive-index variations may, in this case, be provided only on the surface of a fibre or alternatively also extend into the inner volume of the fibre.

For example, a first fibre can be partially ground, scarified, notched or the like on its outer surface, so that the desired refractive-index variation results in the region of these shape changes of the fibres. In this case, a cladding provided on a surface of the first fibre can be locally removed which further benefits lateral decoupling of light components as a result.

Alternatively, the density of the first fibre can be changed locally for example by means of temporary local heating by means of a laser, what is also termed laser grating or fibre grating. Here, an externally located surface of the fibre does not have to be modified, in particular does not need to be changed geometrically and can remain smooth, so that a risk of local dirt deposits is not provoked. Similar effects can be achieved by means of local melting of the surface of a fibre, particularly in the case of polymer fibres.

A further option for local lateral decoupling of light components can be implemented by embedding microscopically small scattering centres or fluorescence centres in light conductive first fibres 9. Scattering centres can in this case be tiny particles preferably made from strongly optically reflective material, for example very small metal particles. Fluorescence centres can for example be particles made from a fluorescent material.

As illustrated in FIG. 1, a plurality of mats 5 can be arranged inside the container 3 of a photobioreactor 1, evenly distributed over a total volume of the container 3. In this case, the mats 5 extend in approximately parallel planes to one another, for example parallel to planes of side walls of the container 3. A spacing between adjacent mats 5 can in this case preferably be smaller than 20 cm, so that over wide areas of the container 3 any location within the container 3 is at a distance of not more than 10 cm from one of the mats 5. In this manner, preferably the entire volume of the nutrient solution accommodated in the container 3 or at least large portions thereof can be evenly supplied with light which was introduced into the container 3 through the common light guide 11 and then irradiated into the nutrient solution by lateral decoupling out of the mats 5.

In addition to the light conductive first fibres 9, the mat 5 has electrically conductive second fibres 11. In the woven fabric of the mat 5 illustrated by way of example in FIG. 2, the electrically conductive second fibres 11 run transversely, particularly essentially perpendicular to the first fibres 9. In this case, the second fibres 11 run essentially parallel to one another.

In the example illustrated, the second fibres 11 are divided into a first subgroup 11', a second subgroup 11" and a third subgroup 11'". The second fibres 11', 11", 11'" of the first, second and third subgroups are arranged in a cyclical pattern. In the example with three subgroups illustrated in FIG. 2, a fibre 11" of the second subgroup is arranged adjacently to a second fibre 11' of the first subgroup and then a fibre 11'" of the third subgroup, before the cycle repeats and a fibre 11' of the first group follows again.

In addition to the mat 5, the mat arrangement 50 has an electric voltage source 30. The voltage source 30 is configured in such a manner that electrical AC voltages are applied at three different electrodes 32, 34, 36, wherein the voltages are phase-shifted by 120° to one another in each case. Each of the second fibres 11', 11", 11'" of one of the three subgroups is electrically connected to one of the three electrodes 32, 34, 36 in each case and electrically insulated with respect to second fibres of different subgroups. Temporally varying electric fields are generated in the vicinity of these second fibres by means of the AC voltages applied at the second fibres 11', 11", 11'", wherein temporally and spatially varying field gradients arise.

Because not only two, but rather at least three different subgroups of second fibres 11', 11", 11'" are provided in the mat 5 and these are correspondingly connected to at least three electrodes 32, 34, 36 with phase-shifted AC voltages applied thereto, electrical field structures that are spatially consecutive, mutually sequenced as it were, can be generated in the form of a travelling electric alternating field, to some extent also termed a "travelling wave". The polyphase current or the polyphase voltage generated by the voltage source 30 can in this case ensure a travelling electric alternating field, similarly to in the case of a for example three-phase electric motor.

A travelling electric alternating field of this type can act on charged particles which are located in the vicinity of the mat 5 and exert a force on the same, in order to therefore move the same in a travel direction 38. In this case, the travel direction 38 runs generally perpendicular to a direction of longitudinal extent of the second fibres 11.

In the example illustrated in FIG. 1, the second fibres 11 run vertically, so that a travel direction 38 approximately parallel to the base of the container 3 of the photobioreactor 1 results. Phototrophic organisms which are often ionised and therefore electrically charged in the basic state or at least in an excited state due to light, can be transported or conveyed along the transport direction 38 due to the electric alternating field generated by the mat 5. In the example illustrated, the phototrophic organisms can therefore be moved from a region on the right side in the container 3 in which these organisms are for example initially fed in successively to a region on the left side in the container 3. During this movement process, the phototrophic organisms are continuously supplied with light exiting from the first fibres 9 of the mat 1 and can therefore mature successively. A region on the left side in the container 3 can be designed as a harvesting region (not specifically illustrated in FIG. 1) from which matured organisms can be removed and supplied to further processing.

In an alternative embodiment, the second fibres 11 can be arranged horizontally. In this case, a travel direction 38 in vertical direction results, so that electrically charged particles, such as for example the phototrophic organisms are either successively conveyed to a top surface of the nutrient solution 2 and there can be fished out, or can successively be conveyed to a base of the container 3 and can there for example be sucked out.

Various possible designs of electrically conductive second fibres 11 are illustrated in FIGS. 3(a)-(d).

Figures 3A, 3B, 3C, 3D:
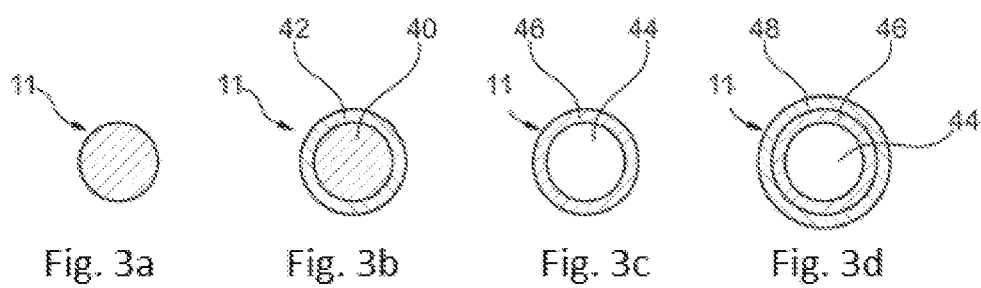
FIGS. 3A to 3D show various designs of fibres for a mat according to an embodiment.

In the example illustrated in FIG. 3(a), the entire fibre 11 consists of an electrically conductive material such as for example carbon or carbon compounds, an electrically conductive polymer (e.g. polyaniline) or a metal.

In the example illustrated in FIG. 3(b), an inner region 40 of the fibre 11 is constructed from an electrically conductive material and encapsulated by an electrically insulating layer 42, for example consisting of a dielectric. The electrically insulating layer 42 can in this case prevent the inner region 40 which is at an electric voltage from directly coming into contact for example with a liquid nutrient solution in a photobioreactor. Whilst a generated electric field can pass through the insulating layer 42, by preventing direct electrical contact between the inner region 40 and the nutrient solution, it is possible to prevent electric currents from flowing and electrolysis processes which may damage the nutrient solution from starting. It is also additionally possible to prevent e.g. metal ions from passing from a metallic core forming the inner region 40 into the nutrient solution and damaging the same.

In the example illustrated in FIG. 3(c), a radially inner region 44 is constructed using an electrically insulating material. For example, this inner region 44 can be constructed in a light conductive manner, for example as a glass fibre. The inner region 44 is surrounded by an outer region 46 made from an electrically conductive material, such as for example a metal layer, a carbon layer or a layer made from an electrically conductive polymer. If the radially inner region 44 is configured to conduct light, it may be advantageous to construct the electrically conductive surrounding region 46 using a transparent material, such as for example tin oxide, zinc oxide or indium oxide, so that the same fibre can be used both for conducting light in the inner region 44 and for conducting electric power in the outer region 46. The surrounding conductive region can also advantageously consist of a transparent electrically conductive polymer, such as e.g. Poly(3,4-ethylenedioxythiophene) (PEDT), for improved adaptation of the refractive index.

In the example illustrated in FIG. 3(d), the structure illustrated in FIG. 3(c) is additionally protected by an outer cover made from an electrically insulating layer 48 and electrically insulated with respect to a surrounding medium, such as a nutrient solution for example. The electrically insulating layer 48 can in this case also be constructed to be optically transparent.

Figure 4:
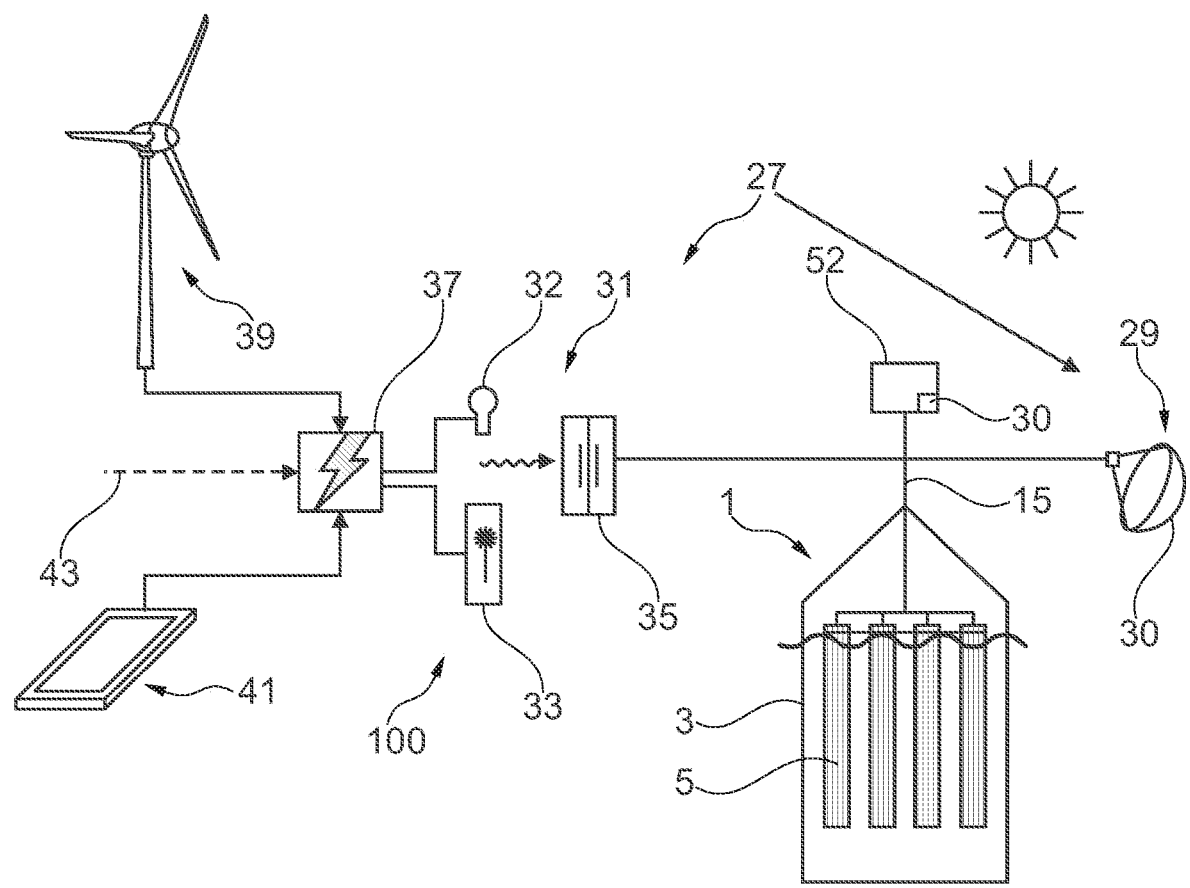
FIG. 4 shows a photobioreactor system according to an embodiment.

FIG. 4 schematically shows a photobioreactor system 100 according to an embodiment. The photobioreactor system 100 has a photobioreactor 1 according to the embodiment and a light source 27. In this case, the light source 27 can have one or a plurality of components for artificially generating light or for collecting naturally generated light and subsequent coupling of this light into a common light guide 15 for supplying the photobioreactor 1.

On the one hand, the light source 27 can be configured as a light source 29 for collecting and coupling sunlight into the light conductive fibres of the photobioreactor 1. Such a light source 29 can for example be constructed as a solar collector 30 with a hollow mirror, which focuses sunlight onto a receiver. Additionally or alternatively, light guide mats for absorbing the sunlight can serve as light source in this sense. The receiver can here be connected to the light guide 11. In this manner, when the sun shines, natural light can be used easily and in an energy-saving manner for illuminating the inner volume of the photobioreactor 1.

Alternatively or additionally, the light source 27 can be configured as a light source 31 for artificially generating and coupling light into light conductive first fibres 9 of the photobioreactor 1. One such artificial light source can for example be configured as an LED 32 or as a laser 33 which irradiates light onto an arrangement 35 made up of a polariser and a screen which in turn is connected to the light guide 15 towards the photobioreactor 1.

The artificial light sources 32, 33 can be supplied by electric power from alternative sources, such as for example by wind power 39 or by solar cells 41 or alternatively by means of conventional power 43. The electric power can in this case be buffer stored by means of for example a buffer battery 37 so that the artificial light source 31 can illuminate the photobioreactor 1 even in the case of insufficient sunshine.

A control unit 52 is furthermore provided in the photobioreactor system 100. This control unit 52 is connected via the light guide 15 to light conductive fibres 9 of the mats 5 in the photobioreactor 1 and configured to feed in light in a targeted fashion. In addition, the control unit 52 also contains the voltage source 30, with the aid of which the suitable electric alternating fields in the mat 5 are generated, in order to permanently circulate the nutrient solution 2 to which phototrophic organisms have been added, and/or to transport the phototrophic organisms in a suitable manner for harvesting, if appropriate.

Embodiments can enable the following advantages, inter alia:

A transport of phototrophic organisms, such as algae for example can be effected in a liquid nutrient medium without external drives, agitators or the like. It may be enough to generate travelling electric alternating fields at the mats 5 provided anyway for feeding in light with the aid of the second electrically conductive fibres 11 provided therein, in order to move the phototrophic organisms. Therefore, no mechanically moved parts are required for mixing or transport. Among other things, this may enable a much more compact design for the photobioreactor. For example, spacing between adjacent mats 5 can be set to be much narrower than was the case for conventional photobioreactors in which the nutrient solution, to which phototrophic organisms had been added had to be stirred for example with the aid of an agitator, because fluid dynamics can be improved substantially by means of the intrinsic drive.

Because the solution to which phototrophic organisms has been added, can be kept moving constantly within the photobioreactor, particularly close to a surface of the mats 5, it is possible to prevent adhesion on the surface of the mats 5 very well which may benefit a long plant service life, can minimise maintenance intervals and can maintain the photon streams within the photobioreactor.

Because smaller spacings are possible between the individual light emitting mats, and as a result for example a level of efficiency during algae production can be increased, in particular a higher photon efficiency can be achieved. At the same time, it is also possible, if appropriate, to work with lower photon densities, which can increase a plant yield in turn. Transport of phototrophic organisms can be realised in a described photobioreactor using outwardly electrically insulated, but internally electrically conductive second fibres or alternatively with outwardly uninsulated second fibres. The outwardly insulated design can have the advantage that very many fewer electric charges can drain away and operation of the transport of the phototrophic organisms can be greatly benefited energetically.

In addition to transport of the phototrophic organisms, an integrated harvesting can also be supported in a particular manner.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

What is claimed is:

1. A mat, comprising:
  a first plurality of first fibres which are light conductive along a first longitudinal direction and are constructed to decouple light conducted in the first longitudinal direction laterally at least somewhat transversely to the first longitudinal direction; and
  a second plurality of second fibres which are electrically conductive along a second longitudinal direction, wherein the second fibres are constructed as carbon fibres or with an electrically conductive polymer; and
  means for generating a travelling electrical wave in the first longitudinal direction.

2. The mat according to claim 1, wherein the first and second fibres are interwoven with one another.

3. The mat according to claim 1, wherein the second fibres are constructed as carbon fibres with an electrically conductive polymer.

4. The mat according to claim 1, wherein the second fibres are constructed in a radially internal region using an electrically insulating material and are coated using an electrically conductive layer in a region that is located radially further out.

5. A mat, comprising:
  a first plurality of first fibres which are light conductive along their longitudinal direction and are constructed to decouple light conducted in the longitudinal direction laterally at least somewhat transversely to the longitudinal direction; and
  a second plurality of second fibres which are electrically conductive along their longitudinal direction, wherein the second fibres are light-conductive in a radially inner region and coated using an electrically conductive and optically transparent layer in a region that is located radially further out.

6. The mat according to claim 1, wherein the second fibres are encapsulated with an electrically insulating layer.

7. The mat according to claim 1, wherein the second fibres are arranged parallel to one another.

8. The mat according to claim 1, wherein the plurality of second fibres has a first, a second, and a third subgroup of second fibres, wherein the subgroups are electrically insulated from one another.

9. The mat according to claim 8, wherein the plurality of second fibres of the first, second and third subgroup are arranged in a cyclical pattern.

10. A light guide mat for use in a container of a photobioreactor, the mat comprising:
  a plurality of light-conductive fibers configured to conduct light in a first longitudinal direction, wherein each light-conductive fiber has at least one decoupling region configured to radiate a portion of the light transversely from the light-conductive fiber;
  a plurality of electrically-conductive fibers interwoven with the light-conductive fibers to form the light guide mat, wherein each electrically-conductive fiber is configured to conduct an electrical current in a second longitudinal direction, wherein the plurality of electrically-conductive fibers includes a first fiber subgroup, a second fiber subgroup, and a third fiber subgroup which are electrically insulated from one another; and
  means for generating a travelling electrical wave in the first longitudinal direction.

11. The light guide mat according to claim 10, wherein the decoupling region comprises a locally curved portion of the first light-conductive fiber.

12. The light guide mat according to claim 10, wherein the decoupling region comprises a local refractive-index variation formed in the light-conductive fiber.

13. The light guide mat according to claim 10, wherein the decoupling region comprises a fiber grating having a local fiber-density variation.

14. The light guide mat according to claim 10, wherein each of the electrically-conductive fibers comprises a light-conducting core configured to conduct light in the second longitudinal direction and an electrically-conductive layer disposed over the light-conducting core and configured to conduct an electrical current in the second longitudinal direction, wherein the electrically-conductive layer is optically transparent such that a portion of the light conducted in the light-conducting core can radiate transversely from the electrically-conductive fiber.

15. The light guide mat according to claim 14, wherein each of the electrically-conductive fibers further comprise an electrically-insulating layer disposed over the electrically-conductive layer, wherein the electrically-insulating layer is optically transparent such that a portion of the light conducted in the light-conducting core can radiate transversely from the electrically-conductive fiber.

16. The light guide mat according to claim 10 wherein the first fiber subgroup, the second fiber subgroup, and the third fiber subgroup are arranged in a cyclical pattern.

17. The light guide mat according to claim 10 wherein the means for generating the travelling electrical wave in the first longitudinal direction comprises:
  a first electrode electrically connected to the first fiber subgroup, a second electrode electrically connected to the second fiber subgroup and phase-shifted by 120° to the first electrode, and a third electrode electrically connected to the third fiber subgroup and phase-shifted by −120° to the first electrode and by 120° to the second electrode; and
  a voltage source configured to generate three respective individual currents through the first, second and third electrodes.

18. The light guide mat of claim 17 wherein the first fiber subgroup, the second fiber subgroup, and the third fiber subgroup are arranged in a cyclical pattern.

* * * * *